United States Patent
Julien (10) Patent No.: US 9,682,526 B2
(45) Date of Patent: Jun. 20, 2017

(54) RADIO FREQUENCY WELDABLE MULTILAYER TUBING AND METHOD OF MAKING THE SAME

(75) Inventor: Christian Julien, Camarillo, CA (US)

(73) Assignee: Meissner Filtration Products, Inc., Camarillo, CA (US)

( * ) Notice: Subject to any disclaimer, the term of this patent is extended or adjusted under 35 U.S.C. 154(b) by 821 days.

(21) Appl. No.: 12/244,230

(22) Filed: Oct. 2, 2008

(65) Prior Publication Data

US 2009/0087606 A1    Apr. 2, 2009

Related U.S. Application Data

(60) Provisional application No. 60/977,018, filed on Oct. 2, 2007.

(51) Int. Cl.
| | |
|---|---|
| *B32B 27/08* | (2006.01) |
| *B32B 1/08* | (2006.01) |
| *B32B 27/40* | (2006.01) |
| *A61M 39/08* | (2006.01) |
| *B32B 27/30* | (2006.01) |
| *A61M 39/14* | (2006.01) |

(52) U.S. Cl.
CPC .............. *B32B 1/08* (2013.01); *A61M 39/08* (2013.01); *B32B 27/08* (2013.01); *B32B 27/304* (2013.01); *B32B 27/306* (2013.01); *B32B 27/40* (2013.01); *A61M 39/146* (2013.01); *B32B 2307/7244* (2013.01); *B32B 2597/00* (2013.01); *Y10T 428/1379* (2015.01); *Y10T 428/1383* (2015.01); *Y10T 428/1393* (2015.01)

(58) Field of Classification Search
USPC ..... 428/35.7, 138, 35.2, 121, 517, 36.7, 213, 428/423.1, 500, 515, 36.9
See application file for complete search history.

(56) References Cited

U.S. PATENT DOCUMENTS

| | | |
|---|---|---|
| 4,714,650 A | 12/1987 | Obayashi et al. |
| 4,803,102 A | 2/1989 | Raniere et al. |
| 5,419,374 A | 5/1995 | Nawrot et al. |

(Continued)

FOREIGN PATENT DOCUMENTS

| | | |
|---|---|---|
| CN | 1147447 A | 4/1997 |
| EP | 0 699 520 A1 | 3/1996 |

(Continued)

OTHER PUBLICATIONS

Invitation to Pay Additional Fees, and Where Applicable, Protest Fee and Communication Relating to the Results of the Partial International Search dated May 9, 2011, for International Application No. PCT/US2008/011426, Filed Oct. 2, 2008; 6 Pages.

(Continued)

*Primary Examiner* — Ellen S Wood
(74) *Attorney, Agent, or Firm* — Lewis Roca Rothgerber Christie LLP (57) ABSTRACT

A RF weldable tubing is provided. The tubing has inner layer including a PVDF copolymer, or an ethylene alpha-olefin homopolymer, or an ethylene alpha-olefin polymer that may include a grafted polyethylene. The tubing may have an inter gas barrier layer sandwiched between the outer layer and an outermost layer including a TPU copolymer. The inter gas barrier layer may include an EVOH copolymer. A method of making such a tubing is also provided.

62 Claims, 6 Drawing Sheets

(56) References Cited

U.S. PATENT DOCUMENTS

| | | | |
|---|---|---|---|
| 5,645,904 A * | 7/1997 | Woo et al. | 428/35.7 |
| 5,910,138 A | 6/1999 | Sperko et al. | |
| 7,011,873 B2 | 3/2006 | Brule et al. | |
| 2002/0112950 A1 | 8/2002 | Topolkaraev et al. | |
| 2003/0031891 A1 | 2/2003 | Fields | |
| 2003/0225201 A1 * | 12/2003 | Yamana et al. | 524/589 |
| 2004/0023037 A1 | 2/2004 | Baumert et al. | |
| 2004/0121099 A1 | 6/2004 | Brule et al. | |
| 2004/0241482 A1 * | 12/2004 | Grah et al. | 428/518 |
| 2005/0037165 A1 | 2/2005 | Ahern et al. | |
| 2005/0050854 A1 | 3/2005 | Zambaux | |
| 2005/0136205 A1 | 6/2005 | Stoppelmann et al. | |
| 2005/0175843 A1 | 8/2005 | Johnson | |
| 2005/0218075 A1 | 10/2005 | Graetz et al. | |
| 2006/0013977 A1 | 1/2006 | Duke et al. | |
| 2006/0019650 A1 | 1/2006 | Kedem | |
| 2006/0160952 A1 * | 7/2006 | Chou et al. | 525/191 |
| 2006/0243666 A1 | 11/2006 | Jenkins et al. | |
| 2006/0246008 A1 | 11/2006 | Jenkins et al. | |
| 2006/0246244 A1 | 11/2006 | Jenkins et al. | |
| 2006/0246537 A1 | 11/2006 | Jenkins et al. | |
| 2006/0251858 A1 * | 11/2006 | Thomas et al. | 428/138 |
| 2007/0044906 A1 * | 3/2007 | Park | 156/272.2 |
| 2008/0261050 A1 | 10/2008 | Hartzel et al. | |
| 2009/0202759 A1 | 8/2009 | O'Brien et al. | |

FOREIGN PATENT DOCUMENTS

| | | |
|---|---|---|
| EP | 1 214 897 A2 | 6/2002 |
| EP | 1 738 896 A1 | 1/2007 |
| JP | 8-142151 A | 6/1996 |
| JP | 2001-193872 A | 7/2001 |
| WO | WO 93/14810 | 8/1993 |
| WO | WO 97/42020 | 11/1997 |
| WO | WO 97/45258 | 12/1997 |
| WO | WO 00/13895 | 3/2000 |
| WO | WO 01/64436 A1 | 9/2001 |
| WO | WO 02/053360 A2 | 7/2002 |
| WO | WO 02/094911 A2 | 11/2002 |
| WO | WO 2004/039582 A1 | 5/2004 |
| WO | WO 2004/039584 A1 | 5/2004 |
| WO | WO 2004/048086 A2 | 6/2004 |
| WO | WO 2005/115753 A1 | 12/2005 |
| WO | WO 2006/040206 A1 | 4/2006 |
| WO | WO 2006/119053 A1 | 11/2006 |
| WO | WO 2007/078972 A2 | 7/2007 |
| WO | WO 2008/005744 A2 | 1/2008 |

OTHER PUBLICATIONS

PCT International Search Report and Written Opinion of the International Searching Authority dated Aug. 2, 2011, for International Application No. PCT/US2008/011426, Filed Oct. 2, 2008 (18 pages).

PCT International Preliminary Report on Patentability dated Aug. 18, 2011, for International Application No. PCT/US2008/011426, Filed Oct. 2, 2008 (11 Pages).

* cited by examiner

RADIO FREQUENCY WELDABLE MULTILAYER TUBING AND METHOD OF MAKING THE SAME

CROSS-REFERENCE TO RELATED APPLICATION

This application claims priority to and the benefit of U.S. Provisional Application No. 60/977,018 filed Oct. 2, 2007 the entire contents of which are incorporated herein by reference.

BACKGROUND

An important aim of the ongoing research in flexible polymer tubing is to provide a high-strength, transparent, sterilizable, disposable, leak-free, inert fluid path for conveying pharmaceutical and biological fluids. A further aim of ongoing research is to provide flexible polymer tubing that is weldable using radio frequency (RF).

Desired attributes of polymer tubing used in the fabrication of flexible disposable container assemblies and fluid paths for pharmaceutical purposes include: ability to weld using RF; clarity; flexibility; endurance; toughness; impact and kink resistance; smooth bore; antistatic; chemical inertness; gas barrier; resistance to change during gamma ($\gamma$) sterilization and biological compatibility. Additionally, flexible thermoplastic-elastomeric tubing used in the fabrication of disposable container assemblies and fluid paths for conveying pharmaceutical raw materials and pharmaceutical products should be essentially free of leachable and extractable material and essentially free of shedded particles to avoid contamination of the transported material and essentially free of any animal derived materials to avoid concerns with respect to transmissible spongiform encephalopathies (TSEs).

While there are flexible polymer tubing materials available for conveying pharmaceutical and biological products, there is a need for a high purity flexible tubing that is RF weldable and not costly to produce.

SUMMARY

In an exemplary embodiment a RF weldable tubing is provided including an outer layer and an immediately adjacent inner layer. The outer layer includes a thermoplastic polyurethane (TPU) copolymer. In yet a further exemplary embodiment, the inner layer has a dielectric loss factor (DLF) value of about or greater than 0.05. In another exemplary embodiment, the inner layer includes a polyvinylidene fluoride (PVDF) copolymer. The PVDF copolymer in one exemplary embodiment includes hexafluoropropylene (HFP). In a further exemplary embodiment, the inner layer includes an ethylene alpha-olefin homopolymer. In yet a further exemplary embodiment, the inner layer includes an ethylene alpha-olefin polymer which may include grafted polyethylene (PE). In another exemplary embodiment, the grafted polyethylene has a weight content ranging from about 1 to about 45 wt % of a total ethylene alpha-olefin copolymer weight. In another embodiment, the grafted polyethylene has a weight content ranging from about 5 to about 25 wt % of a total ethylene alpha-olefin copolymer weight. In yet another exemplary embodiment, the grafted polyethylene is selected from a group consisting of ethylene butyl acrylate (EBA), ethylene methyl acrylate (EMA), and ethylene vinyl acetate (EVA). In a further exemplary embodiment a RF weldable tubing, the tubing further includes an inter gas barrier layer and an outermost layer, where the inter gas barrier layer is disposed between the outer layer, immediately adjacent to the inner layer and the outermost layer. Both the outer layer, immediately adjacent to the inner layer and the outermost layer include a TPU copolymer. In yet a further exemplary embodiment, the inter gas barrier layer includes an ethylene vinyl acetate-vinyl alcohol copolymer (EVOH) copolymer.

In an exemplary embodiment a RF weldable tubing is provided. The tubing includes an inner layer, a gas barrier layer, and a first outer layer including a TPU copolymer, the first outer layer being between the gas barrier layer and the inner layer. The tubing may also include an adhesive tie layer attaching the outer layer to the gas barrier layer. The gas barrier layer may include an EVOH copolymer. In an exemplary embodiment, the inner layer has a DLF value of about or greater than 0.05. In another exemplary embodiment, the inner layer includes a PVDF copolymer. The PVDF copolymer in an exemplary embodiment includes HFP. In one exemplary embodiment, the PVDF copolymer has a HFP content of less than or equal to 25 wt % of a total PVDF copolymer weight. In another exemplary embodiment, the PVDF copolymer has a HFP content ranging from about 10 wt % to about 20 wt % of a total PVDF copolymer weight. In yet another exemplary embodiment, the PVDF copolymer has a HFP content of about 15 wt % of a total PVDF copolymer weight. In a further exemplary embodiment, the inner layer includes an ethylene alpha-olefin homopolymer. In yet a further exemplary embodiment, the inner layer includes an ethylene alpha-olefin polymer which may include grafted polyethylene. The grafted polyethylene may have a weight content ranging from about 1 to about 45 wt % of a total ethylene alpha-olefin copolymer weight. The grafted polyethylene may also have a weight content ranging from about 5 to about 25 wt % of a total ethylene alpha-olefin copolymer weight. In one exemplary embodiment, the grafted polyethylene is selected from a group consisting of ethylene butyl acrylate, ethylene methyl acrylate, and ethylene vinyl acetate. In a further exemplary embodiment, the outer layer includes a polyester-based TPU copolymer. In yet another exemplary an adhesive tie layer is disposed between the first outer layer and the inner layer. In yet a further exemplary embodiment, the tubing further includes a second outer layer such that the gas barrier layer is between the first outer layer and second outer layer. In one exemplary embodiment, the first outer layer and second outer layer have different thicknesses. In another exemplary embodiment, the inner layer and first outer layer and second outer layer have different thicknesses. In another exemplary embodiment, the first outer layer is different from the second outer layer. In yet another exemplary embodiment, the tubing includes a first adhesive tie layer attaching the first outer layer to the gas barrier layer and a second adhesive tie layer attaching the second outer layer to the gas barrier layer. In an exemplary embodiment, the second outer layer includes a TPU copolymer.

In another exemplary embodiment, a RF weldable tubing is provided including a first layer that is RF weldable, a second layer attached to the first layer, the second layer including a TPU copolymer, and a third layer including an EVOH copolymer. The tubing may also include a first adhesive tie layer between the first and second layers. In yet another exemplary embodiment, the tubing also includes a fourth layer attached to the third layer. In a further exemplary embodiment, the tubing further includes a first adhesive layer between the second and third layers, and a second adhesive layer between the third and fourth layers. The tubing may also include a third adhesive layer between the first and second layers. In one exemplary embodiment, the fourth layer includes a TPU copolymer. In yet another exemplary embodiment, the fourth layer is different from the second layer.

In yet another exemplary embodiment a RF tubing is provided including a first layer including a PVDF copolymer, and a second layer attached to the first layer, the second layer including a TPU copolymer. In one exemplary embodiment, the first layer has a DLF value of about or greater than 0.05. In another exemplary embodiment, the PVDF copolymer includes HFP. In yet another exemplary embodiment, the tubing further includes a tie layer between the first and second layers. In an exemplary embodiment, the first layer defines an inner surface of the tubing.

In a further exemplary embodiment, a RF weldable tubing is provided including a first layer including an ethylene alpha-olefin polymer, and a second layer attached to the first layer, the second layer including a TPU copolymer. In yet another exemplary embodiment, the ethylene alpha-olefin polymer includes grafted polyethylene. A tie layer may be disposed between the first and second layers. In a further exemplary embodiment, the tie layer defines an inner surface of the tubing.

In yet a further exemplary embodiment, a RF weldable tubing is provided including a first layer including an ethylene alpha-olefin homopolymer, and a second layer attached to the first layer, the second layer including a TPU copolymer. In one exemplary embodiment, an adhesive tie layer is disposed between the first layer and the second layer. In another exemplary embodiment, the first layer defines an inner surface of the tubing.

In yet another exemplary embodiment, a RF weldable tubing is provided including a first inner layer that is RF weldable, a second layer over the first layer, the second layer including a TPU copolymer, a third layer attached the second layer, the third layer including an EVOH copolymer, a fourth layer attached to the third layer, the fourth layer including a TPU copolymer, the third layer being sandwiched between the second and fourth layers, and a fifth layer over the fourth layer. In a further exemplary embodiment, the first layer includes a material selected from the group of materials consisting essentially of PVDF copolymers, ethylene alpha-olefin homopolymers, and ethylene alpha-olefin polymers that include a grafted polyethylene. In another exemplary embodiment, the fifth layer includes a material selected from the group of materials consisting essentially of PVDF copolymers, ethylene alpha-olefin homopolymers, and ethylene alpha-olefin polymers that include a grafted polyethylene.

DETAILED DESCRIPTION

In the following detailed description, only certain exemplary embodiments of the present invention are shown and described, by way of illustration. As those skilled in the art would recognize, the invention may be embodied in many different forms and should not be construed as being limited to the embodiments set forth herein.

The term "disposable" as used herein may include any item designed for or capable of being disposed of after use, whereas use may be a one-time or multiple-use as required by the pharmaceutical manufacturing process without the need to sterilize the entire disposable container or fluid path more than one time.

The term "conveying" as used herein includes collecting and dispensing of fluids, such as pharmaceutical raw materials and pharmaceutical products, while providing physical containment of materials and products transported, protection of conveyed materials and products from environmental ingress and protection of the environment and operators from egress of conveyed materials and products.

The term "tubing" as used herein, may include any hollow, usually cylindrical body of polymer material, for conveying or containing fluids. The term can mean singular or plural.

The term "containers" as used herein refers to pillow, rectangular, square, conical and cylindrically shaped bags assembled with flexible RF weldable multilayer tubing for collection, dispensing, storing, processing, and shipping of pharmaceutical raw materials and pharmaceutical products. The container can be open at the top or can be closed. The container may include access ports which can be located anywhere in the container. The inner volume of the container can be made to accommodate research and development scale operations or commercial production scale operations. Exemplary containers incorporating ports are shown in U.S. Patent Publication No. US2008/0199645, published on Aug. 21, 2008 based on application Ser. No. 12/069,187, filed on Feb. 8, 2008, the contents of which are fully incorporated herein by reference. Typically the volume of a container will be at least 10 mL, but preferably at least 100 mL. However, sizes of the container ranging from 10 L to 10,000 L are also possible. Small containers can be used without support structure, while a rigid outer support structure can be used for larger containers. The containers may be disposable or otherwise.

The terms "inner," "outer," and "outermost" are relative terms used to denote the relative location of various tubing layers and not the exact location. For example, an "outer" layer or an "outermost" layer of a tubing is not necessarily an external layer of such tubing.

The phrase "fluid paths" as used herein refers to any single piece of tubing or multiple tubing segments interconnected by means of ports, adapters, fittings, filters, valves, instruments, such as disposable sensors, to form manifolds or assemblies for conveying of pharmaceutical raw materials and pharmaceutical products. The fluid paths can be connected to disposable containers or can be connected to rigid wall recipients, including but not limited to bottles, vessels, tanks, and totes.

The phrase "container assemblies" as used herein refers to any combination of at least one container and at least one fluid path attached to the inside or the outside of said container to form an assembly.

The phrase "pharmaceutical raw materials" as used herein refers to raw and in-process biological fluids such as culture media and nutritional components; buffers; aqueous solutions and salt solutions or combinations thereof of varying pH, such as those used in dialysis, chromatography, crystallization, purification; processing solutions composed of either acids, alkali or antifoam agents; water; sanitizing and cleaning detergents; chaotropic solutions and buffers of varying pH for protein refolding, adjuvants, biological materials such as cells, cell debris, cellular components, viruses, antigens; and aliphatic and aromatic organic solvents, such as those used in chemical synthesis, chromatography, crystallization, and extraction.

The phrase "pharmaceutical products" as used herein refers to pharmaceutical and biological intermediate, bulk, purified, formulated and final manufactured products.

The phrase "essentially free of leachable and extractable materials" as used herein means there is either no leachable or extractable material in the flexible RF weldable multilayer tubing used in the fabrication of disposable container assemblies and fluid paths or the amount of leachable and extractable material is so low as to not adversely affect the conveyed fluid or product.

The phrase "essentially chemically inert" as used herein means that the flexible RF weldable multilayer tubing used in the fabrication of container assemblies and fluid paths, as per the required concentration and temperature, be chemically compatible with and resistant to the conveyed fluid or product including the ability to resist swelling, crazing or otherwise withstand attack from fluids or products.

The phrase "essentially free of shedded particles" as used herein means that the RF weldable multilayer tubing used in the fabrication of container assemblies and fluid paths does not shed particles, or that the amount of shed particles is so low as to not adversely affect the conveyed fluid or product.

The phrase "essentially does not absorb proteins and lipids" as used herein means that the RF weldable multilayer tubing used in the fabrication of container assemblies and fluid paths does not absorb proteins and lipids or the amount of absorbed proteins and lipids is so low as to not adversely affect the conveyed fluid or product.

The phrases "leak-free", "no leakage", "fluid containment" and "fluid integrity", as used herein are synonymous and can be used interchangeably.

The phrases "free of any animal derived materials" and "animal derivative free" or "animal derived component free (ADCF)" are synonymous and can be used interchangeably.

The phrases "essentially chemically inert", "essentially free of leachable and extractable materials", "essentially does not absorb proteins and lipids" and "essentially does not shed particles" together determine the "product integrity" and can not be used interchangeably.

The phrase "gas barrier" as used herein refers to a barrier that at least significantly restrains gas passage but may or may not completely block gas passage.

The present invention provides for a novel RF weldable multilayer tubing that may be used in the fabrication of clear and flexible container assemblies and fluid paths to convey fluids or products such as pharmaceutical raw materials and pharmaceutical products.

The RF weldable multilayer tubing of the present invention may be used in the fabrication of container assemblies and fluid paths that can resist mechanical stresses resulting from forces to the tubing such as pressure, shear and compression typically encountered during fluid transport.

In various embodiments, the RF weldable multilayer tubing of the present invention, is used in the fabrication of container assemblies and fluid paths that essentially do not absorb proteins and lipids to avoid loss of conveyed product therein. In addition, the inventive tubing is essentially chemically inert, essentially free of leachable and extractable materials, free of any animal derived materials, and RF weldable.

RF weldability refers to sealing of a RF active polymer to a portion of itself or to another material using electromagnetic energy, where the electromagnetic energy is typically at 27.1 MHz. RF active means a material susceptible to dielectric activation energy at approximately 27.1 MHz, the application of which includes rapid heating of the material.

Dielectric loss factor (DLF) is an excellent tool to screen materials for RF weldability and is calculated by multiplying a material's dielectric constant (DC) by its dielectric dissipation factor (DDF) (or loss tangent). The DC and DDF are readily determined by instrumented dielectric testing methods according to the ASTM D150 test standard.

Typically a material with a DLF of less than 0.05 is considered as RF inactive. While a DLF of about 0.05 to about 0.1 is considered as weakly RF active, and a DLF above 0.2 is considered to be very RF active. While a DLF of about 0.05 or greater may produce satisfactory results, it is preferred that a material with a DLF greater than 0.1 is used. More often a DLF of greater than 0.2 is preferred in order to obtain sufficient sealing energy.

RF welding offers several performance advantages over heat sealing. RF welding allows the energy to be concentrated at the RF active layer, thus eliminating a need to transfer heat through an entire tubing wall structure. This advantage becomes more evident with increasing tubing wall thicknesses, particularly for tubing with wall thicknesses of more than 0.1 inches.

Thermal sealing often requires longer contact time, particularly for thick wall tubing, to permit the thermal transfer through the tubing wall to the bonding interface. In contrast, RF welding parameters do not correlate with tubing thickness.

RF welding has another advantage over thermal sealing. When a multilayer tubing contains a thermally sensitive polymer that may soften, such polymer may also shrink, or degrade upon heating. As a result, welding by thermal heating can subject tubing to structural degradation, compromising the quality of the weld.

Another advantage of RF welding is that tubing containing RF susceptible materials in a first layer immediately adjacent to a second layer can be welded by transferring thermal energy to the second layer through the first layer to RF weld the second layer.

An exemplary embodiment tubing of the present invention is a RF weldable tubing now described with reference to FIGS. 1A and 1B, which illustrates an exemplary embodiment multilayer tubing 100 according to the present invention.

In the exemplary embodiment, multilayer tubing 100 is a two-layer tubing structure having one outer elastomeric layer 20 directly adhered or bonded to one inner thermoplastic layer 10 preferably without the use of an adhesive tie layer. In this exemplary embodiment, the outer layer 20 provides flexibility and additional tensile strength to the resulting tubing and provides for or enhances RF welding capability of the inner layer 10. In this exemplary embodiment, the inner thermoplastic layer 10 is the product contact layer and the outer elastomeric layer 20 is the layer exposed to the external environment.

Another exemplary embodiment tubing of the present invention is a RF weldable tubing now described with reference to FIGS. 2A and 2B, which illustrates an exemplary embodiment multilayer tubing 200 according to the present invention.

In the exemplary embodiment, multilayer tubing 200 is a four-layer tubing structure having one inter gas barrier layer 30 directly adhered or bonded between an outer elastomeric layer 20 immediately adjacent to a thermoplastic inner layer 10 and an outermost elastomeric layer 40, preferably without the use of adhesive tie layers, and where the outer layer 20 is directly adhered or bonded to the thermoplastic inner layer 10 preferably without the use of an adhesive tie layer. In this exemplary embodiment, the elastomeric layers 20 and 40 provide flexibility and additional tensile strength to the resulting tubing and the outer elastomeric layer 20 provides for or enhances RF welding capability of the inner layer 10. In this exemplary embodiment, the inner thermoplastic layer 10 is the product contact layer and the outermost elastomeric layer 40 is the layer exposed to the external environment.

Exemplary embodiments of the multilayer tubing 100 and 200 of the current invention may be fabricated in an inner diameter (ID) ranging from about 0.10 to about 2 inches and an outer diameter (OD) ranging from about 0.13 to about 2.5 inches, and a wall thickness ranging from about 0.015 to about 0.25 inches.

The fluid product contact layer requires several specific attributes including clarity, flexibility, resistance to change during sterilization by gamma (γ) irradiation. In addition, a fluid product contact layer, in one exemplary embodiment, is abrasion resistant and essentially does not shed particles, is essentially free of leachables and extractable materials to avoid contamination of the conveyed fluid, essentially chemically inert and compatible with fluids such as pharmaceutical raw materials and pharmaceutical products, and ADCF. In one exemplary embodiment the fluid product contact layer essentially does not absorb proteins and lipids to avoid loss of conveyed product. In one exemplary embodiment the product contact layer should be preferably composed of a material that can also be injection molded to manufacture tube ports, such as those to access fluid stored or processed within a container, connectors, and fittings to form disposable assemblies and fluid paths having the same product contact material.

Generally, PVDF can be used as a fluid product contact layer in tubing used in the fabrication of container assemblies and fluid paths because it is relatively pure. PVDF consisting of fluoro monomers vinylidene fluoride (VF2) is widely accepted in the food and pharmaceutical industry and is an excellent choice for the fluid product contact layer due to its known low extractables profile, high chemical resistance, thermal stability, abrasion resistance, resistance to gamma (γ) rays, biological compatibility and ease of processability. However, PVDF by itself is not a good candidate for RF welding. In addition it can be expensive, and not transparent and not flexible when made into tubing with a certain wall thickness, particularly with a thickness that is greater than 0.05 inches.

In a effort to take advantage of the desired PVDF quality while providing an fluid product contact layer that is RF weldable, flexible and having sufficient clarity, and resistant to change during sterilization by gamma (γ) irradiation in one exemplary embodiment, the tubing of the present invention includes a fluid product contact layer, i.e., an inner layer, including a PVDF and HFP. The PVDF copolymer with HFP (hereinafter "PVDF copolymer") provides the necessary RF welding capability.

In addition to providing RF weldability, an exemplary embodiment PVDF copolymer used to make the fluid product contact layer of the tubing of present invention does not require anti-oxidants, plasticizers, heat stabilizers or processing aids such as lubricants and is essentially free of leachable and extractable materials. Further, it has high chemical resistance, good abrasion characteristics, essentially does not absorb proteins and liquids and is animal derivative free, making it an excellent candidate for the inner layer for fluid product contact in tubing used in the fabrication of container assemblies and fluid paths.

While HFP provides RF weldability, it can lower the material strength and melting temperature of the resulting copolymer. If a large amount of HFP is used, the resulting tubing can have low tensile strength, not be heat resistant to temperatures as high as 121° C., and autoclavable and be more expensive. On the other hand, if too little amount of HFP is used, the resulting tubing can be inflexible, less transparent and not RF weldable. Therefore, the amount of HFP has to be determined based on the desired tensile strength, clarity, and RF weldability.

According to various aspects of embodiments of the present invention, only a small amount of HFP is needed to make a PVDF copolymer tubing or multilayer tubing RF weldable. Similarly, any film, port, connector or fitting used in the fabrication of RF weldable container assemblies and fluid paths can be RF welded to one another and to each other if the welding layer of these components includes a PVDF copolymer with HFP. Preferably, all of the film, port, connector, fitting or tubing to be RF welded together all have the same PVDF copolymer with HFP in the welding layer and having the same HFP weight percentage content.

Accordingly, in one exemplary embodiment, inner layer 10 comprises a PVDF copolymer in multilayer tubing 100 or 200 and may serve as the fluid product contact layer when used in the fabrication of container assemblies and fluid paths. The inner layer 10 has a wall thickness ranging from about 1% to about 35% of the total multilayer tubing 100 or 200 wall thickness. Preferably the inner layer 10 has a wall thickness ranging from about 5% to about 15% of the total wall thicknesses of multilayer tubing 100 or 200.

In one embodiment, the PVDF copolymer of inner layer 10 has less than 25 of its wt % derived from HFP. In another embodiment, the PVDF copolymer of inner layer 10 has between about 10 to about 20 its wt % of derived from HFP. In yet another embodiment, the PVDF copolymer inner layer has about 15 of its wt % derived from HFP.

In an exemplary embodiment of the present invention, a PVDF copolymer with a HFP content of about 15 wt % is preferred for tubing fabrication because at this concentration the PVDF copolymer containing tubing may be used in the fabrication of container assemblies and fluid paths as it provides all the necessary fluid and product integrity properties needed for conveying pharmaceutical raw materials and pharmaceutical products. For instance, a PVDF copolymer containing tubing with 15 wt % of HFP has good clarity, is autoclavable, is capable of undergoing steaming processes which are typically used for sterilization purposes, is biological compatible, is essentially free of leachable and extractable materials, is essentially free of shedded particles, is essentially chemically inert, it essentially does not absorb proteins and lipids, and at the same time is RF weldable. It is also easier to manufacture by reducing the cycle time required for melting and extruding the PVDF copolymer as compared to the PVDF homopolymer.

In an exemplary embodiment, the PVDF copolymer has a specific gravity from about 1.76 to about 1.82. In another embodiment, the PVDF copolymer has a melting temperature between 115° C. and about 175° C., preferably of between about 125° C. and about 155° C., and more preferably between about 130° C. and about 145° C. In one embodiment, the PVDF copolymer has a melt viscosity of about 600 to about 1500 Pa·s; and a melting point of about 117° C. to about 145° C., preferably of about 130° C. Non-limiting examples of such PVDF copolymers include Arkema Kynar® Flex 2500 copolymer, Arkema Kynar® Flex 2750 copolymer, Arkema Kynar® Flex 2800 copolymer, Arkema Kynar® Flex 2850 copolymer and Solvay Hylar® 21508-0001.

These exemplary embodiments are for illustrative purpose only and it is to be understood that the same or equivalent materials may be used in different embodiments that are also intended to be encompassed within the spirit and scope of the invention. For example, other commercially available PVDF copolymers were also considered and have been thought to give similar results such as Solef® and Hylar® from Solvay, especially relevant are the grades with low crystallinity, and especially PVDF copolymers with a Shore D hardness between about 50 and about 75.

While PVDF copolymers as described above have all the desirable fluid and product integrity properties and are excellent candidates for making fluid product contact layers, they still can be cost inhibitive. Accordingly, various exemplary embodiments of the present invention an inner layer 10 is provided that is indirectly RF weldable in that such layer requires that it be adjacent to an RF susceptible layer. Such inner layer is composed of thermoplastic polyolefins, such as ethylene alpha-olefin polymers. Exemplary RF susceptible layers, i.e. outer layers, include layers made with a TPU copolymer. With this exemplary embodiment, heat is transferred from the RF susceptible outer layer 20 immediate adjacent to the inner layer 10 for welding such inner layer.

Suitable thermoplastic polyolefins can be selected from a group including homopolymers and copolymers of alpha-olefins containing 2 to 20 carbon atoms, and preferably copolymers of alpha-olefins containing 2 to 10 carbons, and more preferably copolymers of alpha-olefins containing 4 to 8 carbons. Such copolymers are commonly referred to as ultra-low density polyethylenes (ULDPE) or linear low density polyethylenes (LLDPE) or low density polyethylene (LDPE) and are indirectly RF weldable in a multilayer tubing 100, and 200 of the current invention.

In an exemplary embodiment of the present invention, a ULDPE, or LLDPE, or LDPE inner fluid product contact layer containing tubing may be used in the fabrication of container assemblies and fluid paths as it provides all the necessary fluid and product integrity properties needed for conveying pharmaceutical raw materials and pharmaceutical products. For instance, a LDPE inner fluid product contact layer tubing has good clarity, good flexibility, is resistant to change during sterilization by gamma (γ) irradiation, is biological compatible, is essentially free of leachable and extractable materials, is essentially free of shedded particles, is essentially chemically inert, and at the same time is indirectly RF weldable. In another exemplary embodiment, inner layer 10 comprises ethylene alpha-olefin copolymers, which are produced using a single-site catalyst such as metallocene catalyst and with resins that do not contain slip agents and antiblock, such as MarFlex® from Chevron-Philips and Purell from Basell.

In an exemplary embodiment the ethylene alpha-olefin polymer includes a grafted polyethylene that provides the resulting polymer with RF welding capability. In one embodiment the ethylene alpha-olefin copolymer includes a grafted polyethylene content ranging from about 1 to about 45 wt % of a total ethylene alpha-olefin copolymer weight. In another embodiment, the ethylene alpha-olefin polymer includes a grafted polyethylene with a weight content ranging from about 5 to about 25 wt % of a total ethylene alpha-olefin copolymer weight. Suitable grafted polyethylene can be selected from a group consisting of EBA, EMA, and EVA.

The outer and outermost layers require several specific attributes including clarity, flexibility, non-tackiness, toughness, puncture resistance, resistance to change during sterilization by gamma (γ) irradiation and biological compatible. They may also be antistatic. The outermost layer may also need to be printable.

In addition, an outer layer, immediately adjacent to an inner layer, in one exemplary embodiment is resistant to change during sterilization by gamma (γ) irradiation, is flexible, is tough, is clear, and is essentially free of leachables and extractable materials, and is ADCF to avoid contamination of the conveyed product. In one embodiment the outermost or outer layer exposed to the external environment is resistant to change during sterilization by gamma (γ) irradiation, is flexible, is tough, is clear, is puncture and abrasion resistant, it essentially does not shed particles and it essentially chemically inert to safeguard against accidental spills.

In addition, an outer layer immediately adjacent to the inner fluid product contact layer is often provided to further improve the structural integrity, further improve the tensile strength and toughness and provides for RF welding capability or further improve the RF weldability of the inner fluid product contact layer. Referring back to FIGS. 1A and 1B, outer layer 20 typically has a wall thickness ranging from about 65% to about 99% of the total wall thickness of a multilayer tubing 100. Preferably, outer layer 20 has a wall thickness ranging from about 85% to about 95% of the total thickness of a multilayer tubing 100. Referring back to FIGS. 2A and 2B, outer layer 20 and outermost layer 40 combined typically have a total wall thickness ranging about 30% to about 98% of the total wall thickness of a multilayer tubing 200. Preferably, outer layer 20 and outermost layer 40 combined have a total wall thickness ranging about 70% to about 90% of the total thickness of a multilayer tubing 200. In an exemplary embodiment, the outer layer 20 and outermost layer 40 both are composed of a TPU copolymer.

TPU copolymer is a widely accepted copolymer for use in the food industry and used extensively in medical devices and is a good choice for the outer and outermost layers due to its high tensile strength, rubber-like elasticity, transparency, exceptional structural memory, high resilience, adhesive properties, ease of processability, resistance to change during gamma (γ) sterilization, and low temperature flexibility. In addition, TPU does not require plasticizers and can be formulated animal derived component free.

Not only does a TPU copolymer enhance the structural integrity and tensile strength of the inner layer, a TPU copolymer has a DLF of about 0.4 and therefore converts RF energy to thermal energy, thereby generating heat that is transferred to the fluid product contact layer and useful in the welding process. In other words, outer layers composed of a TPU polymer and immediately adjacent to a fluid product contact layer can shorten overall welding cycle time.

Accordingly, an inner fluid product contact layer that is composed of a PVDF homopolymer may be RF weldable if an immediately adjacent TPU-containing outer layer is provided. However, an inner fluid product contact layer containing PVDF homopolymer may not be as desirable as it is not flexible and lacks clarity. Applicants have discovered that when an inner fluid product contact layer is composed of PVDF copolymer containing less than 10 wt % HFP, use of an immediate adjacent outer layer composed of TPU copolymer results in an inner fluid product contact layer that is RF weldable. When an inner fluid product contact layer composed of PVDF copolymer containing more than 10 wt % HFP, an immediately adjacent TPU-containing outer layer may also be used but is not necessary, as the inner fluid product contact layer by itself is RF weldable to itself or to other RF weldable materials. Of course, use of a TPU-containing outer layer immediately adjacent to an inner layer is desired in a multilayer tubing as it provides the additional tensile strength and RF welding capability to the resulting tubing.

There are various TPU materials that can be used for the outer layers, including TPU copolymers made from aliphatic or aromatic isocyanates, and polyester or polyether polyols, whereby the type of polyols and isocyanates determine the final properties of the TPU copolymer. In an exemplary embodiment, the TPU material for the outer layer and outermost layer in multilayer tubing is an aromatic isocyanate polyether polyol based TPU copolymer with specific gravity from about 1.10 to 1.21 having good clarity and tensile strength, is resistant to change during sterilization by gamma ($\gamma$) irradiation, is biological compatible, is essentially free of leachable and extractable materials, and is abrasion resistant. In an exemplary embodiment, the TPU copolymer has a melt flow rate of about 10 to about 40 g/10 min; a tear strength greater or equal to 65 N/mm, preferably greater or equal to 85 N/mm; and a tensile strength greater than 30 MPa, preferably greater or equal to 45 MPa. Examples of TPU copolymers with such a characteristic include, but are not limited to, Noveon Estane® 58887 and BASF Elastollan® 1185A10.

Another example TPU material that can be used for the outer layer and outermost layer in multilayer tubing is an aromatic isocyanate polyester polyol based TPU copolymer with specific gravity of from about 1.10 to about 1.21 having good clarity and tensile strength, is resistant to change during sterilization by gamma ($\gamma$) irradiation, is biological compatible, is essentially free of leachable and extractable materials, and is abrasion resistant, such as Noveon Estane® 58271, Noveon Estane® 58238, BASF Elastollan® 688A10N and BASF Elastollan® 685A10N. Other commercially available polyester and polyether polyol based TPU copolymers were also considered and thought to give similar results are Pellethane® from The Dow Chemical Company, Texin® from Bayer MaterialScience, and Elastollan® 600 and 1100 series from BASF, and especially TPU copolymers with a Shore A hardness between about 76 and about 91.

Although both polyether and polyester polyol based TPU copolymers are disclosed, a polyester polyol based TPU copolymer may be preferred according to various embodiments of the present invention. It is believed, that a polyester polyol based TPU copolymer provides better adhesion. In contrast, it is believed that a polyether polyol based TPU copolymer does not necessary provide the desired adhesion result with the inner fluid product contact layer composed of PVDF copolymer. It is also believed, that a polyester polyol based TPU copolymer provides better clarity results.

To find an appropriate PVDF-TPU material combination, various PVDF copolymers and TPU copolymers were selected from different suppliers, grades, and physical characteristics, such as melt flow index (MFI) and viscosity to determine suitable PVDF-TPU material combinations that have proper adhesion and sufficient peel strength. The adhesion data of different PVDF-TPU material combinations and the adhesion test method have been previously disclosed in U.S. Patent Publication No. US2008/0199645, published on Aug. 21, 2008 based application Ser. No. 12/069,187, filed on Feb. 8, 2008, the contents of which are fully incorporated herein by reference. In summary, good adhesion between PVDF copolymers and TPU copolymers is achieved whenever Kynar® Flex 2750-01 or Kynar® Flex 2750-13 are used with Noveon Estane® 58271 nat 021 or BASF Elastollan® 685A10N, considered to be equivalent to Elastollan® 688A10N. Further, good adhesion is also achieved whenever Solvay Hylar® 21508-0001 is used with Noveon Estane® 58271 nat 021 or BASF Elastollan® 685A10N, considered to be equivalent to Elastollan® 688A10N. As mentioned previously, the TPU layer is added to promote strength to the inner layer and to provide for RF welding capability or enhance RF weldability of the inner fluid product contact layer.

Generally, materials with similar rheological profile are highly desirable as they may be more suitable for tubing coextrusion. The rheological data of different PVDF and TPU materials have been previously disclosed in U.S. Patent Publication No. US2008/0199645, published on Aug. 21, 2008 based on application Ser. No. 12/069,187, filed on Feb. 8, 2008, the contents of which are fully incorporated herein by reference. In summary, Kynar® Flex 2750-13 is a suitable material as its viscosity profile is closer to the rheological profiles of previously disclosed TPU copolymers indicating greater compatibility with disclosed TPU materials. In addition, Hylar® 21508-0001 has a similar viscosity profile to disclosed TPU copolymers and is considered to be another good candidate for PVDF copolymer selection. Further, disclosed data seem to suggest that in TPU copolymer selection, particularly TPU copolymers that comprise a polyester polyol are important in determining compatibility of different raw materials for multilayer tubing coextrusion, as these have better adhesion results, and as a result do not require the use of an adhesive tie layer to bond certain PVDF copolymers.

Figure 2A:
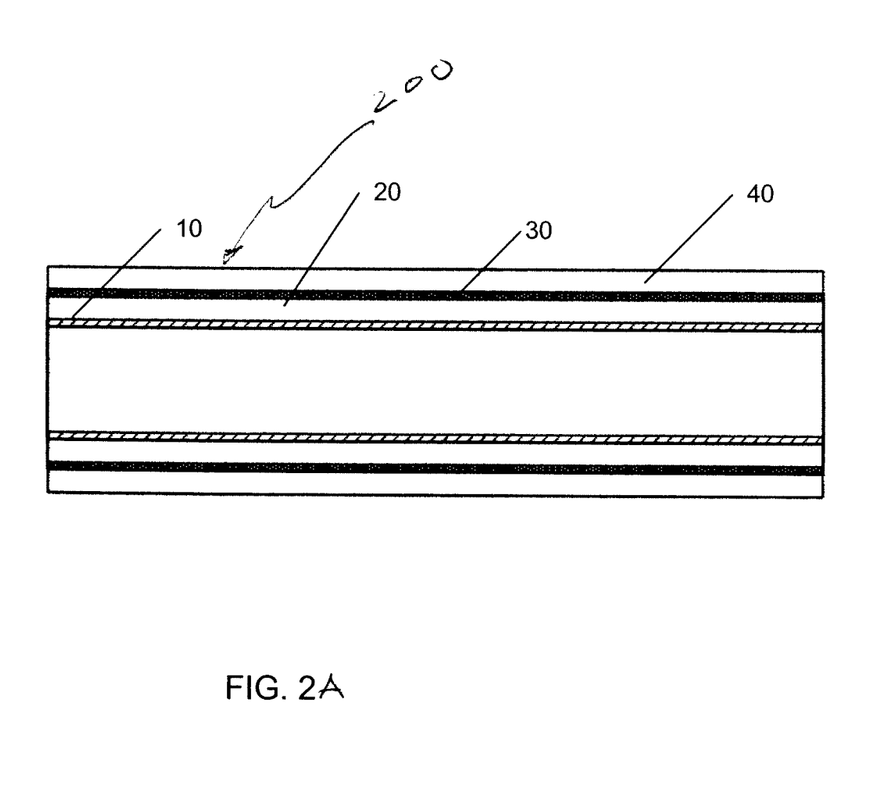
FIGS. 2A and 2B schematically depict longitudinal and transverse cross-sectional views, respectively, of a four-layer tubing comprising a gas barrier layer according to an exemplary embodiment of the present invention.
Figure 2B:
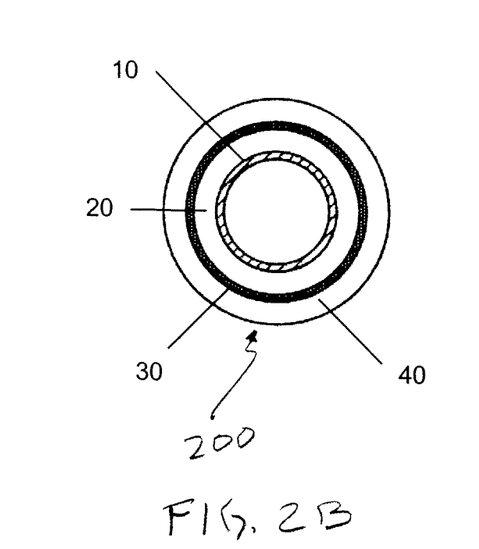

Referring to FIGS. 2A and 2B, the inter gas barrier layer 30 is sandwiched between the outer layer 20 and outermost layer 40 of the multilayer tubing 200 preferably without the use of adhesive tie layers. The function of the inter gas barrier layer is to provide for resistance to transmission of gases, such as water vapor, oxygen and carbon dioxide beyond what is achievable using solely an inner fluid product contact layer and an outer layer immediately adjacent to the inner layer. In one embodiment the inter gas barrier layer has several specific attributes including clarity, flexibility, biological compatibility and resistance to change during sterilization by gamma ($\gamma$) irradiation. In another embodiment the inter gas barrier layer is ADCF.

Inter gas barrier layer 30 has a wall thickness ranging form about 1% to about 35% of the total wall thickness of multilayer tubing 200. Preferably, inter gas barrier layer 30 has a wall thickness ranging form about 5% to about 15% of the total thickness of a multilayer tubing 200.

The material for inter gas barrier layer 30 is normally ethylene vinyl acetate-vinyl alcohol copolymer (EVOH). In one embodiment, the EVOH of inter gas barrier layer 30 includes about 32% mol % ethylene vinyl acetate (EVA) copolymer, with specific gravity of about 1.20. In another embodiment, the EVOH copolymer used has a melt flow rate of about 3.7 to about 5 g/10 min. Examples of materials with such characteristics include commercially available EVAL® F101A non-lubricated, EVAL® F101B lubricated, EVAL® F104A non-lubricated, and EVAL® F104B lubricated copolymer from EVAL Company of America. Again, these exemplary embodiment materials are for illustrative purpose only and it is to be understood that the same or equivalent materials may be used in other embodiments that are also intended to be encompassed within the spirit and scope of the invention.

Figure 5:
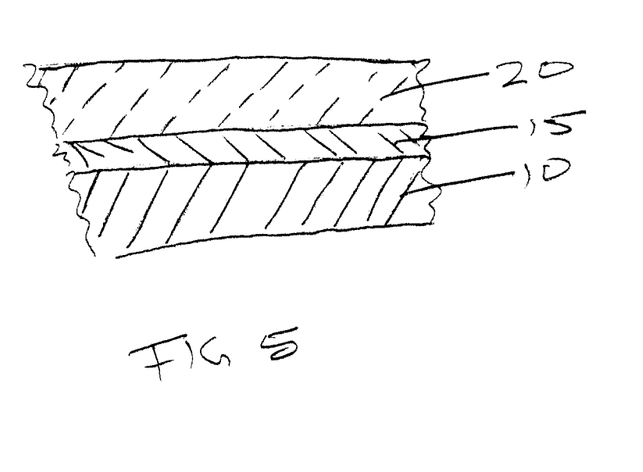
FIG. 5 is a schematic cross-sectional view of two layers of a tubing bonded with an adhesive tie layer.

Although adhesive tie layers are not shown in the exemplary embodiments to render a three-layer multilayer tubing 100, in one embodiment, and to render a five-layer multilayer tubing 200, in another embodiment, an adhesive tie layer can be present between the inner fluid product contact layer 10 and the outer layer 20. In another embodiment an adhesive tie layer can be present between the inter gas barrier layer 30 and the outer layer 20 or between the inter gas barrier layer 30 and the outermost layer 40 to render a five-layer multilayer tubing 200. In yet another embodiment an adhesive tie layer can be present between the inter gas barrier layer 30 and the outer layer 20 and between the inter gas barrier layer 30 and the outermost layer 40 to render a six-layer multilayer tubing. In yet another embodiment an adhesive tie layer can be present between the inter gas barrier layer 30 and the outer layer 20, and between the inter gas barrier layer 30 and the outermost layer 40, and between the inner fluid product contact layer 10 and the outer layer 20. These adhesive tie layers are typically polyurethane adhesives or maleic anhydride modified polyolefins such as LLDPE. An example of a tie layer 15 between inner layer 10 and outer layer 20 is schematically shown in FIG. 5.

Figure 1A:
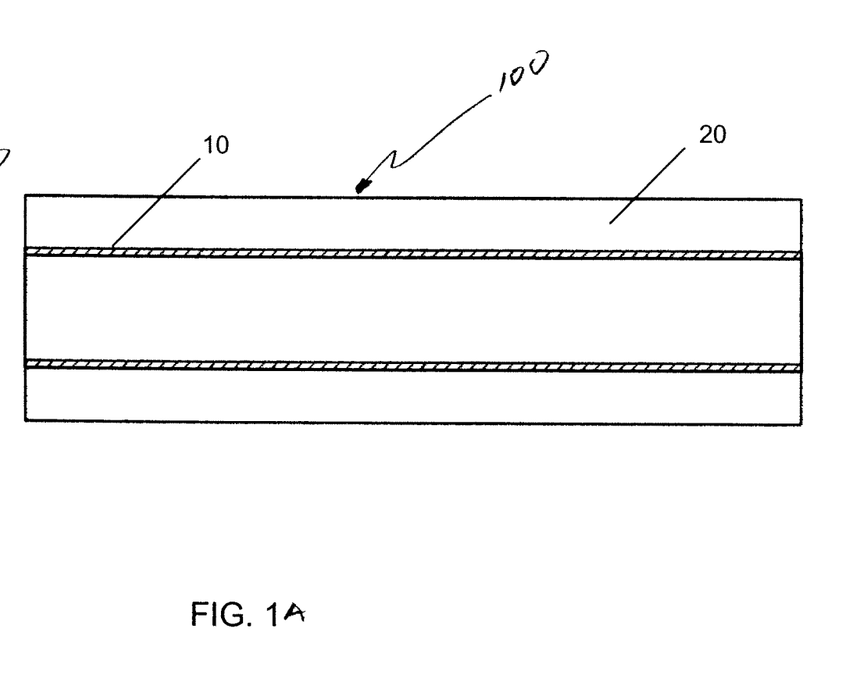
FIGS. 1A and 1B schematically depict longitudinal and transverse cross-sectional views, respectively, of a two-layer tubing according to an exemplary embodiment of the present invention.
Figure 1B:
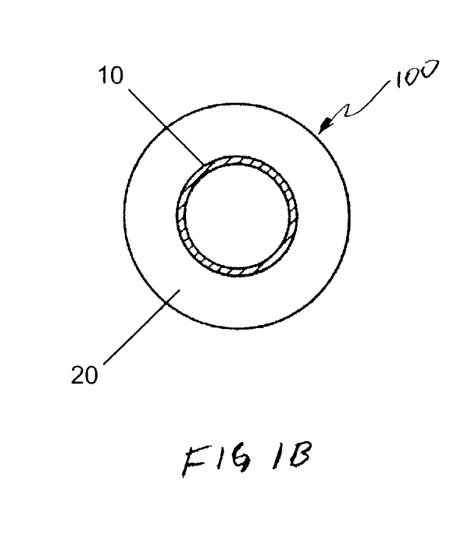

In an exemplary embodiment, the resulting tubing 100 of FIGS. 1A and 1B and 200 of FIGS. 2A and 2B has a flexible body and excellent clarity. It has a smooth bore, is not tacky and is leak free. It is also antistatic. Due to the use of a PVDF copolymer in the inner layer in the flexible multilayer tubing 100 or 200 of the current invention, the inner product contact layer, i.e., the inner layer, is RF weldable. It also has excellent performance at low temperature, remains flexible and does not become brittle when stored at about −80° C. When PVDF copolymer is used for the inner fluid product contact layer, i.e. the inner layer, the tubing 100 or 200 of the current invention also has broader chemical resistance, improved levels of leachables and extractable materials, improved levels of nonspecific protein and lipid absorption, and reduced particle shedding, compared to conventional tubing used in the same applications. When a homopolymer or copolymer of alpha-olefins containing 2 to 10 carbons is used for the inner fluid product contact layer, i.e., the inner layer, the tubing 100 or 200 of the current invention has broader chemical resistance and improved levels of leachables and extractable materials compared to conventional tubing used in the same applications. In another embodiment the tubing 100 and 200 can be made to experience minimum fatigue and permanent tensile set by selecting a TPU in the outer layer exposed to the external environment with increased hardness for example larger than 88 Shore A.

Accordingly, a PVDF copolymer containing inner product contact layer multilayer tubing 100 or 200 of the present invention may be used in the fabrication of container assemblies and fluid paths for conveying pharmaceutical raw materials and pharmaceutical products where a low leachables and extractables profile, a low non specific protein and lipid absorption, tubing clarity and barriers to both water vapor and gas are highly desired. In addition, multilayer tubing 100 or 200 may be used in the fabrication of container assemblies and fluid paths that are essentially chemically inert to most acids, bases, salts, and aliphatic, aromatic and halogenated hydrocarbons, alcohols, aldehydes, ketones, esters, and in particular to organic solvents routinely used in pharmaceutical manufacturing.

Accordingly, a homopolymer or copolymer of alpha-olefins having 2 to 10 carbons containing inner product contact layer multilayer tubing 100 or 200 of the present invention may be used in the fabrication of container assemblies and fluid paths for conveying pharmaceutical raw materials and pharmaceutical products where a low leachables and extractables profile, tubing clarity and barriers to both water vapor and gas are highly desired. In addition, multilayer tubing 100 or 200 may be used in the fabrication of container assemblies and fluid paths that are essentially chemically inert to most acids, bases, salts, alcohols, aldehydes, and esters routinely used in pharmaceutical manufacturing.

Various embodiments of the RF weldable tubing of the current invention are specifically formulated to meet USP Class VI, EP and ISO 10993 requirements. In some embodiments the RF weldable tubing of the current invention is specifically formulated to omit any animal derived materials. In other embodiments, the PVDF copolymer containing inner product contact layer multilayer tubing is free of leachable and extractable aluminum, calcium and zinc. Further in an exemplary embodiment, no plasticizers, oils or surfactants, or other processing aids, such as anti-oxidants and heat stabilizers are used. Therefore, in such an exemplary embodiment, the PVDF copolymer containing inner product contact layer multilayer tubing of the current invention is free or at least essentially free of leachable and extractable materials, such as plasticizers, anti-oxidants and heat stabilizers.

The multilayer tubing of the present invention can be sterilized by gamma (γ) radiation. Applicants have discovered that there is no visual or significant physical property change when the multilayer tubing is exposed to high levels of gamma radiation of up to 50 kGy. In other embodiments of the present invention, the multilayer tubing structure can withstand high temperature greater than 60° C. for extended periods of time, e.g., for even 24 hours, without compromising fluid integrity.

Exemplary embodiments of the flexible tubing of the current invention have excellent strength to wall thickness ratios allowing for significant down gauging. In addition, they also have excellent tensile properties, puncture resistance and hysteresis properties. The tubing also has excellent seam peel strength when RF welded together or to other polymers. The seam peel strength in exemplary embodiments is greater than 80% of the tensile strength of the tubing. The seam peel strength is an indicator of bond adhesion resulting from the RF welding process.

Figure 3A:
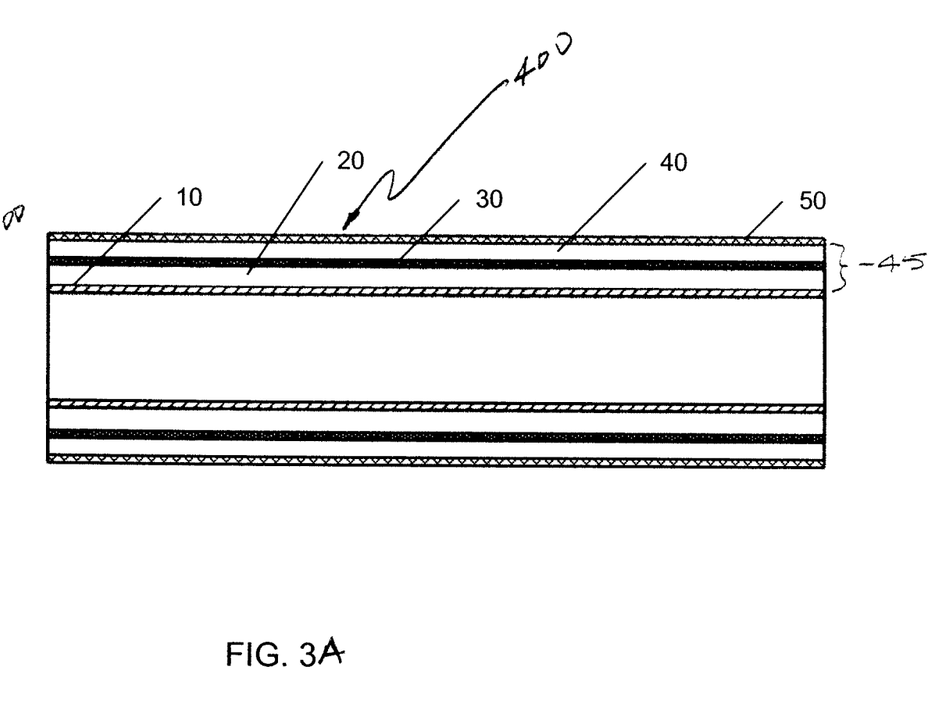
FIGS. 3A and 3B schematically depict longitudinal and transverse cross-sectional views, respectively, of a five-layer tubing comprising a gas barrier layer according to an exemplary embodiment of the present invention.
Figure 3B:
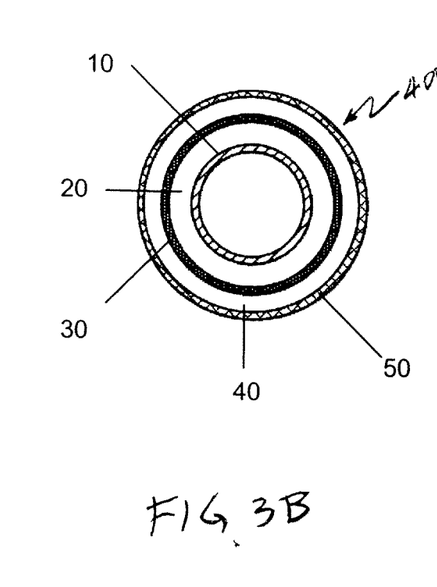

Although the above described exemplary embodiments are mostly directed toward a two-layer or a four-layer tubing, applicants believe other multilayer tubing constructions are also possible based on desirable properties of PVDF and TPU copolymers that applicants discovered. For example, a multilayer tubing 400 having an inter layer 30 composed of EVOH copolymer, sandwiched between outer layer and outermost layers 20, 40, each composed of TPU copolymer is desirable, as the sandwich of layers outer, inter and outermost layers provides a core layer structure 45 that is both strong and a barrier to gas, as show in FIGS. 3A and 3B. This core layer structure, in turn may be sandwiched between an inner layer 10 and an outermost layer 50, composed of a PVDF copolymer, or an ethylene alpha-olefin homopolymer, or an ethylene alpha-olefin polymer that includes a grafted polyethylene of the present invention. This core layer structure in other exemplary embodiments may be sandwiched between other types of inner and outermost layers. In other exemplary embodiments, the outermost layer 50 is not included.

In one embodiment, the RF weldable multilayer tubing of the present invention is used in the fabrication of container assemblies and fluid paths, capable of withstanding temperatures as low as −80° C. for holding pharmaceutical raw materials and pharmaceutical products. A tubing that does not become brittle when stored at temperatures as low as −80° C. is required for container assemblies holding biological materials such as cells as well as protein solutions. In one exemplary embodiment, the tubing does melt and retains its chemical and mechanical properties in container assemblies used for culture of extremophiles at temperatures as high as +90° C. In another exemplary embodiment, the RF weldable multilayer tubing of the present invention used in the fabrication of container assemblies and fluid paths is capable of withstanding temperatures as high as 121° C. For example, in one embodiment, the tubing does not to melt and retains its chemical and mechanical properties required for steam connectivity to ancillary stainless steel tanks and processing equipment at temperatures as high as +121° C. for up to 30 minutes. The inventive tubing may be used in the fabrication of container assemblies and fluid paths to convey pharmaceutical raw materials and pharmaceutical products at elevated temperatures.

Another aspect of the present invention is directed towards a method of manufacturing a RF weldable multilayer tubing 200. The invention is now described with reference to FIG. 4, which illustrates a simplified manufacturing line arrangement 300 for making a RF weldable multilayer tubing 200.

Figure 4:
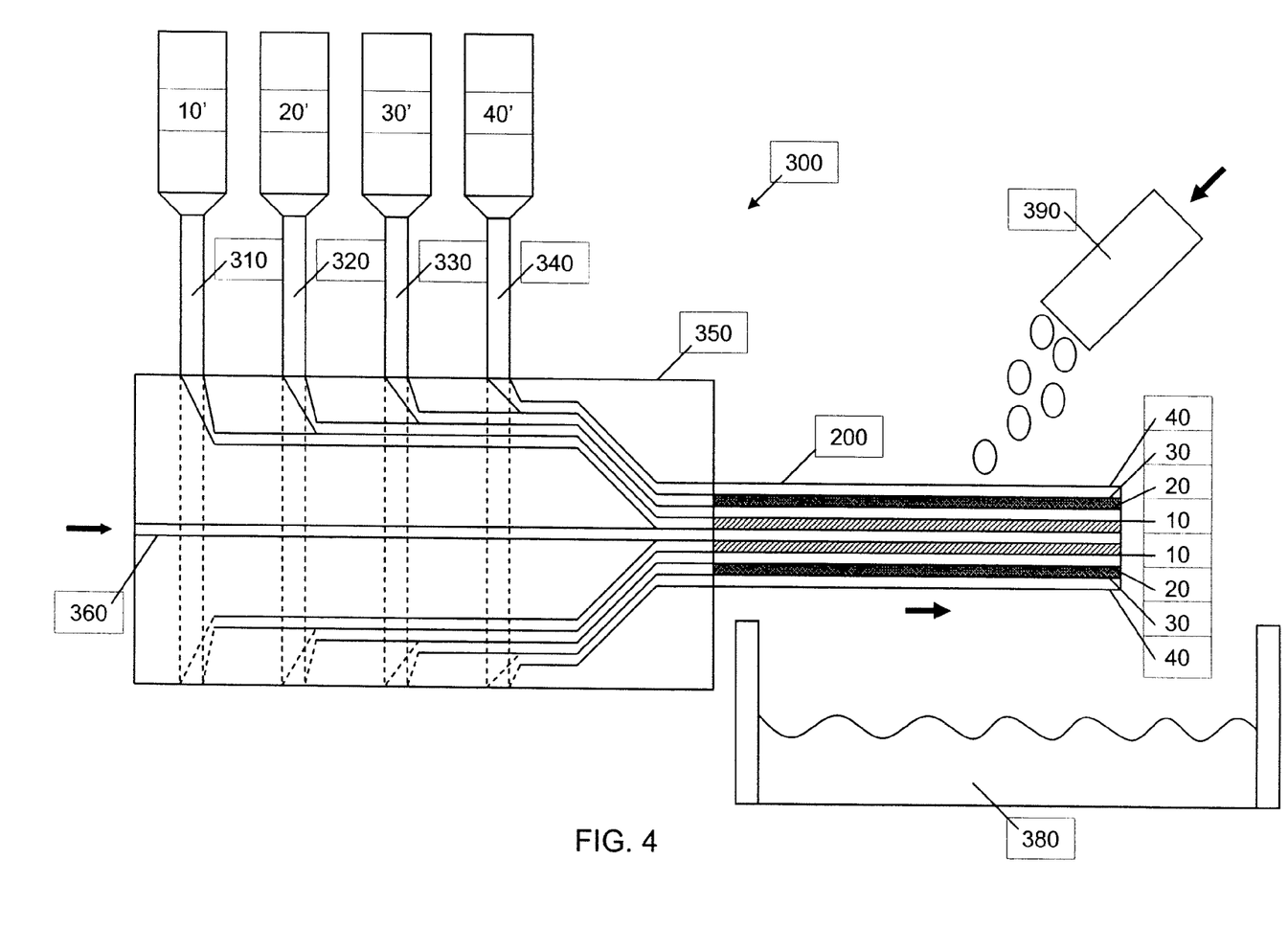
FIG. 4 is a schematic illustration of a tubing coextrusion line arrangement used to manufacture a four-layer tubing according to an exemplary embodiment of the present invention.

The inner fluid product contact layer composition 10', the outer layer composition 20', the inter gas barrier layer composition 30' and the outermost layer composition 40' are fed simultaneously into their respective extruders 310, 320, 330, 340 into a coextrusion tubing die 350 having an air inlet 360, providing air form a preferably sterile filtered air source, to form a multilayer tubing 200 composed of inner layer 10, then outer layer 20, then inter gas barrier layer 30 and then outermost layer 40, allowed to cool by being passed through a waterbath 380 (schematically shown in FIG. 3) which is continuously replenished with cold water 390, and taken up on coils or spools and cut to various lengths (not shown).

It should be noted that the multilayer tubing 200 of different ID and OD can be manufactured, whereas each specific combination of ID and OD requiring typically a different coextrusion tubing die 350.

Also, while a four-layer tubing manufacturing process is shown, it should be understood that a two-layer tubing 100 or other multilayer tubing, such as a three-layer, can also be manufactured by this process by omitting or changing certain layer compositions, starting from the inner fluid product contact layer, i.e., the inner layer composition and ending at the outermost layer composition.

Figure 6:
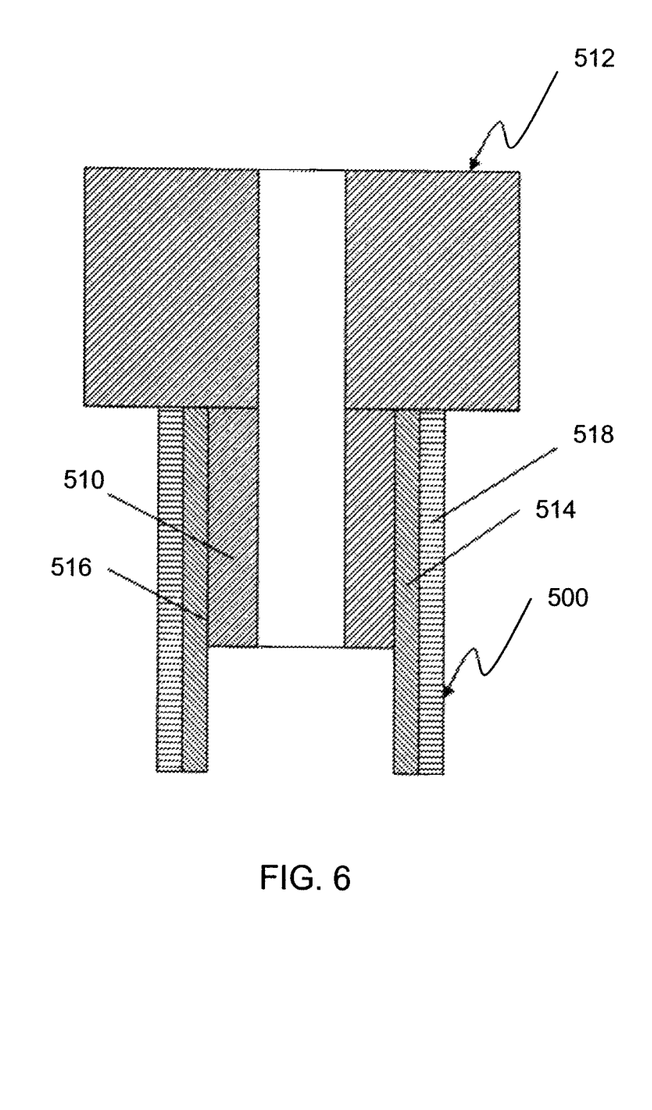
FIG. 6 is a schematic cross-sectional view of a tubing according to an exemplary embodiment of the present invention RF welded to a port of a container.

The five-layer tubing 400, the four-layer tubing 200 or two-layer tubing 100 structure manufactured by the disclosed process or similar process such as sequential extrusion, molding or comolding can be used in the fabrication of container assemblies, bag assemblies and fluid paths. The tubing can be used in the fabrication of container assemblies to form fluid paths by RF welding, heat welding, or by other conventional mechanical attachment or retention methods. With reference to FIG. 6 tube-to-port welds can be achieved by first sliding tubing 500 of the present invention, having an inner layer 514 and an outer layer 518, over a geometrically suitable tube port 510 extending from a container boat port 512, weldable to a container, to form a tight mechanical fit and then RF welding the inner layer 514 of the tubing 500 to the outer surface 516 of the tube port 510 using a RF port sealer which is capable of applying electromagnetic energy across the tubing layers 518 and 514 and across the tube port 510. Tube seals can be achieved by first clamping the tubing to compress the inner layer of the wall together and then RF weld the inner layer of the tubing to itself to seal off the flow through such tubing.

EXAMPLES

Certain examples and test data for multilayer tubing according to the present invention are depicted in Table 1 and Table 2.

Table 1 shows various physical characteristics of monolayer tubing made of typical styrene-ethylene-butylene-styrene (SEBS) block copolymers and a multilayer tubing of the present invention. As shown,

TABLE 1

Physical characteristics of SEBS monolayer tubing and PVDF copolymer multilayer tubing

| Properties | Test Method | Units | SEBS Tubing | Example 1 |
|---|---|---|---|---|
| Tubing Manufacturing | | | | |
| Process | | | Extrusion | Coextrusion |
| Electrical | | | | |
| DLF | ASTM D150 | | <0.001 | >0.05 |
| RF weldability | | | No | Yes |
| Physical | | | | |
| Wall thickness | | inches | 0.126 | 0.060 |
| Optical appearance | | | Translucent | Transparent |
| Water absorption | ASTM D570, 23° C., 24 hours | % | 0.2 | 0.7 |
| Sterilization | | | | |
| Gamma (γ) irradiation dose | Dosimeter | kGy | 25-40 | 25-40 |
| Gamma (γ) resistance, color change | Visual inspection | | None to slight yellowing | None |

Example 1 is a two-layer tubing fabricated by coextrusion with a total wall thickness of about 0.060 inches, having a PVDF inner fluid product contact wall thickness, i.e. inner layer thickness of about 0.002 inches or about 3% of the total wall thickness, and a TPU outer layer wall thickness of about 0.058 inches or about 97% of the total wall thickness of tubing 100.

The PVDF inner fluid product contact layer in Example 1 is composed of Arkema Kynar® Flex 2750-13 copolymer with a specific gravity from about 1.78 to about 1.80. It has a melt viscosity of about 736 Pa·s according to ASTM D3835 test standard (230° C., 100 s$^{-1}$) and a melting point of about 130° C.

The TPU outer layer in Example 1 is composed of BASF Elastollan® 688A10N copolymer comprised of an aromatic isocyanate polyester polyol with specific gravity of about 1.21. It has a tensile strength of about 5202 PSI according to ASTM D412 test standard, a tear strength of about 698 lbf/in. according to ASTM D624 (Die C) test standard, and a melt flow rate of about 12.96 g/10 min according to ASTM D1238 test standard (190° C., 8.7 kg).

The SEBS monolayer tubing data in Table 1 and Table 2 are provided for comparison purposes only and should serve to give an indication of how the multilayer tubing of the current invention relates to a typical SEBS monolayer tubing in use today. The data provided on the SEBS monolayer tubing are intended to be representative of typical commercial tubing. Accordingly, the tubing's properties may change slightly depending on the manufacturer and batch tested. Example 1 is RF weldable, while SEBS monolayer tubing is not.

Table 2 shows various tensile properties of comparative SEBS tubing and the exemplary embodiment, Example 1, of the present invention

TABLE 2

Mechanical properties of SEBS monolayer tubing and PVDF copolymer multilayer tubing.

| Mechanical Properties | Test Method | Units | SEBS Tubing | Example 1 |
| --- | --- | --- | --- | --- |
| Tensile strength at 100% strain | ASTM D412 | psi | 230 | 1190 |
| Tensile strength at 300% strain | ASTM D412 | psi | 380 | 1980 |
| Tensile strength at break | ASTM D412 | psi | 1190 | 6080 |
| Elongation at break | ASTM D412 | % | 708 | 490 |
| Compression set at 70° C., 22 hours | ASTM D385 | % | 57 | 60 |

Tensile properties, namely tensile strength, elongation and compression set are often measured in accordance with a laboratory test procedure utilizing a test instrument which applies a load to a specimen. Example 1 provides better results in terms of tensile strength at 100% and 300% strain and at break points with comparable elongation, and compression set, with half its wall thickness.

RF Welding Example

In the exemplary embodiment, the two-layer RF weldable tubing in Example 1 is weldable using a commercially available RF welding apparatus comprising a 200 Watt RF generator and a welding head with build-in clamping feature to hold secure the tubing during the welding process. The RF generator and welding head used are respectively Sebra model 3120 and Sebra model 3806, operated at 100% RF power or dial setting 9.9, RF dwell time dial setting 2.0 and clamp dial setting 0.3, capable of welding the tubing in 13 seconds which represents the total cycle time.

Extruder Process Example

In the exemplary embodiment, the two-layer RF weldable tubing in Example 1 is fabricated by a coextrusion process comprising two extruders 310, 320 and one tubing die. Extruders 310, 320 have three barrel zones Nos. 1-3 respectively (not shown) for conveying, compressing and metering the feed. The feed zone No. 1 is the area where the feed is propelled forward. The compression zone No. 2 is where the root diameter of the screw gradually increases and where the pressure buildup, frictional heat, and melting occur. The metering zone No. 3 is the area where the flow rate of the melt is controlled and fed into the tubing die zone. The compression ratio is the ratio between the depth of flight in the feed zone to the depth of the flight in the metering zone. The tubing tie comprising the multi-layer cross head and core tip provides the compression ratio to enable the fabrication of the two-layer tubing with a thin inner layer to close dimensional tolerances. Typical examples of extruders are Killion KN150, 30:1 L/D single screw extruders and a typical example of a crosshead is Genca Tri-Die. The extruders 310, 320 together with the tubing die and different operating temperatures dictate how feed polymers are extruded through the tubing die.

In the exemplary embodiment, the inner layer of the RF weldable tubing in Example 1 comprises PVDF copolymer and is extruded through extruder 310 with three different barrel zones Nos. 1-3. The set temperatures of barrel zones Nos. 1-3 are at about 170° C. to about 210° C., about 180° C. to about 220° C., and about 190° C. to about 230° C., respectively. Preferably, set temperatures of barrel zones Nos. 1-3 are at about 175° C. to about 205° C., about 185° C. to about 210° C., and about 195° C. to about 225° C., respectively. Set temperatures of adapter and die zone are at about 190° C. to about 230° C., and preferably at about 190° C. to about 225° C.

The outer layer of the RF weldable tubing in Example 1 comprises TPU copolymer and is extruded through extruder 320 with three different barrel zones Nos. 1-3. The set temperatures of barrel zones Nos. 1-3 are at about 160° C. to about 185° C., about 165° C. to about 190° C., and about 170° C. to about 195° C., respectively. Preferably, set temperatures of barrel zones Nos. 1-3 are at about 165° C. to about 180° C., about 170° C. to about 185° C., and about 175° C. to about 190° C., respectively. Set temperatures of adapter and die zone are at about 170° C. to about 205° C., and preferably at about 175° C. to about 200° C.

Although exemplary and preferred embodiments of the invention have been described in the Example and foregoing detailed description, it will be understood that the invention is not limited to the embodiments disclosed, but is capable of numerous rearrangements, material substitutions, and modifications of parts and compositions without departing from the spirit of the invention as defined in the following claims. Therefore, the spirit and the scope of the appended claims should not be limited to the description of the preferred embodiments contained herein.

The invention claimed is:

1. A radio frequency (RF) weldable tubing for receiving a fluid, the RF weldable tubing comprising:
    an inner layer formed from a RF active material susceptible to at least a dielectric activation energy at approximately 27.1 MHz, and defining at least a majority of an inner surface of said tubing for receiving said fluid and for contacting said fluid, the RF active material comprising a polyvinylidene fluoride (PVDF) copolymer;
    a gas barrier layer; and
    a first outer layer comprising a polyester-based thermoplastic polyurethane (TPU) copolymer, said first outer layer being directly laminated to the inner layer and being between the gas barrier layer and the inner layer, wherein said tubing is RF weldable.

2. The RF weldable tubing of claim 1, further comprising an adhesive tie layer attaching the first outer layer to the gas barrier layer.

3. The RF weldable tubing of claim 1, wherein the gas barrier layer comprises an ethylene vinyl acetate-vinyl alcohol (EVOH) copolymer.

4. The RF weldable tubing of claim 1, wherein the PVDF copolymer comprises hexafluoropropylene (HFP).

5. The RF weldable tubing of claim 1, wherein the PVDF copolymer has a HFP content of less than or equal to 25 wt % of a total PVDF copolymer weight.

6. The RF weldable tubing of claim 1, wherein the PVDF copolymer has a HFP content ranging from about 10 wt % to about 20 wt % of a total PVDF copolymer weight.

7. The RF weldable tubing of claim 1, wherein the PVDF copolymer has a HFP content of about 15 wt % of a total PVDF copolymer weight.

8. The RF weldable tubing of claim 1, wherein the inner layer further comprises an ethylene alpha-olefin homopolymer.

9. The RF weldable tubing of claim 1, wherein the inner layer further comprises an ethylene alpha-olefin polymer comprising grafted polyethylene.

10. The RF weldable tubing of claim 9, wherein the grafted polyethylene has a weight content ranging from about 1 to about 45 wt % of a total ethylene alpha-olefin copolymer weight.

11. The RF weldable tubing of claim 9, wherein the grafted polyethylene has a weight content ranging from about 5 to about 25 wt % of a total ethylene alpha-olefin copolymer weight.

12. The RF weldable tubing of claim 9, wherein the grafted polyethylene is selected from the group consisting of ethylene butyl acrylate, ethylene methyl acrylate, ethylene vinyl acetate, and combinations thereof.

13. The RF weldable tubing of claim 1, wherein the PVDF copolymer comprises HFP, and the gas barrier layer comprises an EVOH copolymer.

14. The RF weldable tubing of claim 1, wherein the inner layer further comprises an ethylene alpha-olefin polymer, and the gas barrier layer comprises an EVOH copolymer.

15. The RF weldable tubing of claim 14, further comprising an adhesive tie layer disposed between the first outer layer and the inner layer.

16. The RF weldable tubing of claim 14, wherein the ethylene alpha-olefin polymer comprises grafted polyethylene.

17. The RF weldable tubing of claim 16, wherein the grafted polyethylene has a weight content ranging from about 1 to about 45 wt % of a total ethylene alpha-olefin copolymer weight.

18. The RF weldable tubing of claim 16, wherein the grafted polyethylene has a weight content ranging from about 5 to about 25 wt % of a total ethylene alpha-olefin copolymer weight.

19. The RF weldable tubing of claim 16, wherein the grafted polyethylene is selected from the group consisting of ethylene butyl acrylate, ethylene methyl acrylate, ethylene vinyl acetate, and combinations thereof.

20. The RF weldable tubing of claim 1, further comprising a second outer layer, wherein the gas barrier layer is between the first outer layer and second outer layer.

21. The RF weldable tubing of claim 20, wherein the first outer layer and second outer layer have different thicknesses.

22. The RF weldable tubing of claim 20, wherein the inner layer and first outer layer and second outer layer have different thicknesses.

23. The RF weldable tubing of claim 20, wherein the first outer layer is different from the second outer layer.

24. The RF weldable tubing of claim 20, further comprising a first adhesive tie layer attaching the first outer layer to the gas barrier layer and a second adhesive tie layer attaching the second outer layer to the gas barrier layer.

25. The RF weldable tubing of claim 20, wherein the second outer layer comprises a polyester-based TPU copolymer.

26. The RF weldable tubing of claim 20, wherein the gas barrier layer comprises an EVOH copolymer.

27. The RF weldable tubing of claim 20, wherein the inner layer further comprises an ethylene alpha-olefin homopolymer.

28. The RF weldable tubing of claim 20, wherein the inner layer further comprises an ethylene alpha-olefin polymer comprising grafted polyethylene.

29. A radio frequency (RF) weldable tubing for receiving a fluid, the RF weldable tubing comprising:
a first layer, said first layer of said tubing formed from a RF weldable material being RF weldable at least with an electromagnetic energy at 27.1 MHz, said first layer defining at least a majority of an inner surface of said tubing for receiving said fluid and for contacting said fluid, said RF weldable material comprising a polyvinylidene fluoride (PVDF) copolymer;
a second layer directly laminated to the first layer, the second layer comprising a polyester-based thermoplastic polyurethane (TPU) copolymer; and
a third gas barrier layer comprising an ethylene vinyl acetate-vinyl alcohol (EVOH) copolymer, said gas barrier layer being attached to said second layer.

30. The tubing of claim 29, further comprising a fourth layer attached to the third layer.

31. The tubing of claim 30, further comprising:
a first adhesive layer between the second and third layers; and
a second adhesive layer between the third and fourth layers.

32. The tubing of claim 30, wherein the fourth layer comprises a polyester-based TPU copolymer.

33. The tubing of claim 30, wherein the fourth layer is different from the second layer.

34. A radio frequency (RF) weldable tubing for receiving a fluid, the RF weldable tubing comprising:
a first layer comprising a RF active polyvinylidene fluoride (PVDF) copolymer susceptible to at least a dielectric activation energy at approximately 27.1 MHz, said first layer defining at least a majority of an inner surface of said tubing for receiving said fluid and for contacting said fluid; and
a second layer directly laminated to the first layer, the second layer comprising a polyester-based thermoplastic polyurethane (TPU) copolymer.

35. The RF weldable tubing of claim 34, wherein the PVDF copolymer comprises hexafluoropropylene (HFP).

36. A radio frequency (RF) weldable tubing for receiving a fluid comprising:
a first inner layer formed from a RF weldable material being RF weldable at least with an electromagnetic energy at 27.1 MHz, said RF weldable material comprising a polyvinylidene fluoride (PVDF) copolymer and an ethylene alpha-olefin polymer, said first inner layer defining at least a majority of an inner surface of said tubing for receiving said fluid and for contacting said fluid; and
a second layer directly laminated to the first layer, the second layer comprising a polyester-based thermoplastic polyurethane (TPU) copolymer, wherein the ethylene alpha-olefin polymer comprises grafted polyethylene.

37. A radio frequency (RF) weldable tubing for receiving a fluid, the RF weldable tubing comprising:
- a first inner layer formed from a RF weldable material being RF weldable at least with an electromagnetic energy at 27.1 MHz, said first inner layer defining at least a majority of an inner surface of said tubing for receiving said fluid and for contacting said fluid, said RF weldable material comprising a polyvinylidene fluoride (PVDF) copolymer;
- a second layer directly laminated to the first layer, the second layer comprising a polyester-based thermoplastic polyurethane (TPU) copolymer;
- a third gas barrier layer attached to the second layer, the third layer comprising an ethylene vinyl acetate-vinyl alcohol (EVOH) copolymer;
- a fourth layer attached to the third layer, the fourth layer comprising a TPU copolymer, said third layer being sandwiched between said second and fourth layers; and
- a fifth layer over the fourth layer.

38. The tubing of claim 37, wherein the first layer further comprises a material selected from the group of materials consisting of ethylene alpha-olefin homopolymers, ethylene alpha-olefin polymers that include a grafted polyethylene, and combinations thereof.

39. The tubing of claim 38, wherein the fifth layer comprises a material selected from the group of materials consisting of PVDF copolymers, ethylene alpha-olefin homopolymers, ethylene alpha-olefin polymers that include a grafted polyethylene, and combinations thereof.

40. The tubing of claim 37, wherein the fifth layer comprises a material selected from the group of materials consisting of PVDF copolymers, ethylene alpha-olefin homopolymers, ethylene alpha-olefin polymers that include a grafted polyethylene, and combinations thereof.

41. The RF weldable tubing of claim 1 wherein the inner layer, the gas barrier layer and the first outer layer are coextruded.

42. The RF weldable tubing of claim 29 wherein the first layer, the second layer, and the third layer are coextruded.

43. The RF weldable tubing of claim 29 wherein the first layer and the second layer are coextruded.

44. The RF weldable tubing of claim 36 wherein the first layer and the second layer are coextruded.

45. The RF weldable tubing of claim 37 wherein the first layer, the second layer, the third layer, the fourth layer and the fifth layer are coextruded.

46. A radio frequency (RF) weldable tubing for receiving a fluid, the RF weldable tubing comprising:
- an inner layer, said inner layer defining at least a majority of an inner surface of said tubing for receiving said fluid and for contacting said fluid, the inner layer comprising an RF active material comprising a polyvinylidene fluoride (PVDF) copolymer;
- a gas barrier layer; and
- a first outer layer comprising a polyester-based thermoplastic polyurethane (TPU) copolymer, said first outer layer being directly laminated to the inner layer and being between the gas barrier layer and the inner layer, wherein said tubing is RF weldable.

47. A radio frequency (RF) weldable tubing for receiving a fluid, the RF weldable tubing comprising:
- a first layer comprising a RF active polyvinylidene fluoride (PVDF) copolymer and defining at least a majority of an inner surface of said tubing for receiving said fluid and for contacting said fluid; and
- a second layer directly laminated to the first layer, the second layer comprising a polyester-based thermoplastic polyurethane (TPU) copolymer.

48. The RF weldable tubing of claim 47, wherein the polyvinylidene fluoride (PVDF) copolymer comprises hexafluoropropylene (HFP).

49. The RF weldable tubing of claim 1, wherein said inner layer defines an entirety of said inner surface of said tubing.

50. The RF weldable tubing of claim 29, wherein said first layer defines an entirety of said inner surface of said tubing.

51. The RF weldable tubing of claim 34, wherein said first layer defines an entirety of said inner surface of said tubing.

52. The RF weldable tubing of claim 36, wherein said first inner layer defines an entirety of said first inner surface of said tubing.

53. The RF weldable tubing of claim 37, wherein said first inner layer defines an entirety of said first inner surface of said tubing.

54. The RF weldable tubing of claim 46, wherein said inner layer defines an entirety of said inner surface of said tubing.

55. The RF weldable tubing of claim 47, wherein said first layer defines an entirety of said inner surface of said tubing.

56. The RF weldable tubing of claim 1, wherein the PVDF copolymer comprises hexafluoropropylene (HFP) in an amount less than 10 wt %.

57. The RF weldable tubing of claim 29, wherein the PVDF copolymer comprises hexafluoropropylene (HFP) in an amount less than 10 wt %.

58. The RF weldable tubing of claim 34, wherein the PVDF copolymer comprises hexafluoropropylene (HFP) in an amount less than 10 wt %.

59. The RF weldable tubing of claim 36, wherein the PVDF copolymer comprises hexafluoropropylene (HFP) in an amount less than 10 wt %.

60. The RF weldable tubing of claim 37, wherein the PVDF copolymer comprises hexafluoropropylene (HFP) in an amount less than 10 wt %.

61. The RF weldable tubing of claim 46, wherein the PVDF copolymer comprises hexafluoropropylene (HFP) in an amount less than 10 wt %.

62. The RF weldable tubing of claim 47, wherein the PVDF copolymer comprises hexafluoropropylene (HFP) in an amount less than 10 wt %.

\* \* \* \* \*